United States Patent
Komatsubara et al.

(10) Patent No.: US 9,439,397 B2
(45) Date of Patent: Sep. 13, 2016

(54) ABSORBENT ARTICLE FOR PET

(75) Inventors: Daisuke Komatsubara, Kagawa (JP); Takeshi Ikegami, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 14/007,876

(22) PCT Filed: Mar. 13, 2012

(86) PCT No.: PCT/JP2012/056470
§ 371 (c)(1),
(2), (4) Date: Nov. 27, 2013

(87) PCT Pub. No.: WO2012/132888
PCT Pub. Date: Oct. 4, 2012

(65) Prior Publication Data
US 2014/0090608 A1    Apr. 3, 2014

(30) Foreign Application Priority Data
Mar. 30, 2011 (JP) ................. 2011-075850

(51) Int. Cl.
*A01K 23/00* (2006.01)
*A61F 13/15* (2006.01)

(52) U.S. Cl.
CPC ...... *A01K 23/00* (2013.01); *A61F 2013/15186* (2013.01)

(58) Field of Classification Search
CPC ..... A01K 23/00; A61F 5/4401; A61F 13/49; A61F 13/49014
USPC ............ 119/867–79, 167, 169, 170, 867–69; 604/358, 385.03, 385.23, 385.24, 391, 604/394, 380, 382, 385.09

IPC ............ A01K 23/00; A61F 5/44,13/49, 13/494
See application file for complete search history.

(56) References Cited

U.S. PATENT DOCUMENTS 7,331,945 B2 * 2/2008 Suzuki et al. ......... 604/385.201
7,666,175 B2 * 2/2010 Trennepohl ............. 604/385.28
(Continued)

FOREIGN PATENT DOCUMENTS

| CN | 201701387 U | 1/2011 |
|---|---|---|
| JP | 2004-159592 A | 6/2004 |

(Continued)

OTHER PUBLICATIONS

International Search Report from corresponding PCT application No. PCT/JP2012/056470 dated May 15, 2012 (2 pgs).
(Continued)

*Primary Examiner* — Lisa Tsang
(74) *Attorney, Agent, or Firm* — Brinks Gilson & Lione

(57) ABSTRACT

An absorbent article for pets which includes: a liquid permeable top surface layer; a liquid impermeable back surface layer; and an absorbent core disposed between the top and back surface layers, the absorbent article for pets being configured in a rectangular shape with a pair of end portions facing each other and a pair of side portions facing each other orthogonal to the pair of end portions, the absorbent article for pets being configured to be worn in a state of being wrapped around a waist of a pet, the absorbent article for pets further including first and second solid gather portions that are respectively disposed on the top surface layer side of the pair of side portions and rises up from the top surface layer, in which the first solid gather portion is configured to be easier to lie outward in the width direction of the absorbent article for pets.

7 Claims, 19 Drawing Sheets

(56) References Cited

U.S. PATENT DOCUMENTS

| | | | |
|---|---|---|---|
| 9,023,006 B2* | 5/2015 | Takino et al. | 604/385.29 |
| 2003/0004490 A1* | 1/2003 | Larsson et al. | 604/390 |
| 2004/0127865 A1* | 7/2004 | Mitsui et al. | 604/358 |
| 2005/0061260 A1 | 3/2005 | Hall | |
| 2006/0282055 A1* | 12/2006 | Shiomi | A61F 13/4915 604/385.09 |
| 2007/0149941 A1* | 6/2007 | Ikegami et al. | 604/385.09 |
| 2007/0208316 A1* | 9/2007 | Nakahata et al. | 604/385.02 |
| 2009/0198207 A1* | 8/2009 | Torigoshi et al. | 604/385.29 |
| 2011/0196332 A1* | 8/2011 | Cheng et al. | 604/385.24 |
| 2011/0209675 A1* | 9/2011 | Esperon | 119/868 |

FOREIGN PATENT DOCUMENTS

| | | |
|---|---|---|
| JP | 2007-020533 A | 2/2007 |
| JP | 3141580 U | 4/2008 |

OTHER PUBLICATIONS

Chinese Notice of Reasons for Rejection and English translation from corresponding Chinese application No. 2014082901089310 dated Sep. 3, 2014 (14 pgs).

\* cited by examiner

ABSORBENT ARTICLE FOR PET

RELATED APPLICATION

This application is a 35 U.S.C. §371 national phase filing of International Patent Application No. PCT/JP2012/056470 filed Mar. 13, 2012, to which priority is claimed under 35 U.S.C. §120 and through which priority is claimed under 35 U.S.C. §119 to Japanese Patent Application No. 2011-075850, filed Mar. 30, 2011.

TECHNICAL FIELD

The present invention relates to an absorbent article for pet, which is used in a state of being wrapped around waist of pet such as dog and cat.

BACKGROUND ART

Conventionally, a disposable diaper for pet used for pet such as dog and cat has been proposed. Such a disposable diaper for pet catches feces and urine of pet by covering the anus and the urethral opening positioned between bases of hind legs when being worn.

Some of pets (for example miniature dachshund) have the urethral opening more in front than a position between bases of hind legs. In addition, male dogs have the urethral opening more in front than female dogs. If the disposable diaper for pet is used for pets having the urethral opening more in front than a position between bases of hind legs, the urethral opening may not be covered by the diaper and urine may leak.

Given this, an absorbent article for pet that is used in a state of being wrapped around a pet's waist is proposed, the absorbent article for pet including an absorbent core, a liquid permeable top surface layer disposed on a first face of the absorbent core, and a liquid impermeable back surface layer disposed on a second face of the absorbent core, and being configured in a rectangular shape, in which solid gathers are provided on a pair of sides in the longitudinal direction.

Such an absorbent article for pet configured in a rectangular shape can cover the urethral opening infallibly, regardless of position thereof. In addition, the solid gathers are provided respectively on parts positioned in front of and behind the urethral opening of the pet in a state in which the absorbent article is wrapped around the pet's body, to thereby prevent leakage of urine.

In addition, in order to avoid leakage of urine from between bases of the pet's hind legs, an absorbent article for pet is proposed in which an upright part of a solid gather, which is positioned on a front side of the pet's body, is made longer, and an upright part of a solid gather, which is positioned on a back side of the pet's body, is made shorter (see Patent Document 1).

Upon putting on the absorbent article for pet proposed in Patent Document 1 to a male pet, the upright part of the solid gather positioned on the back side of the pet's body is brought into contact with a base of the pet's sex organ (urinary organ). The solid gather is thus positioned behind the pet's urinary organ, to thereby prevent leakage of urine.

Patent Document 1: Japanese Unexamined Patent Application Publication No. 2007-20533

DISCLOSURE OF THE INVENTION

Problems to be Solved by the Invention

However, in the absorbent article for pet proposed in Patent Document 1, since the upright part of the solid gather positioned on the back side of the pet's body is configured to be shorter, the solid gather is easy to incline inward during putting the absorbent article for pet on the pet. If the solid gather inclines inward, the solid gather no longer can cover the back side of the pet's urinary organ, and urine may leak. In addition, since the absorbent article for pet is put on in a state in which the solid gather with the shorter upright part is in contact with the base of the pet's sex organ, an intense stress is applied to the base of the sex organ and the pet may be physically stressed.

Given this, the present invention is aimed at providing an absorbent article for pet that can cover the back side of the pet's urinary organ appropriately by the solid gather without physically stressing the pet.

Means for Solving the Problems

The present invention relates to an absorbent article for pet including: a liquid permeable top surface layer; a liquid impermeable back surface layer; and an absorbent core disposed between the top surface layer and the back surface layer, the absorbent article for pet being configured in a rectangular shape with a pair of end portions facing each other and a pair of side portions facing each other orthogonal to the pair of end portions, the absorbent article for pet being configured to be worn in a state of being wrapped around a waist of a pet, the absorbent article for pet further including: a first solid gather portion and a second solid gather portion that are respectively disposed on a top surface layer side of the pair of side portions and uprise from the top surface layer, in which the first solid gather portion is configured to easily lie outward in a width direction of the absorbent article for pet.

The first solid gather portion and the second solid gather portion are preferably configured to include: a pair of side sheets that are disposed on the top surface layer side of the pair of side portions, an outer edge of which is joined with the top surface layer or the back surface layer and at least a part of an inner edge of which is a free end; and an elastic member that is attached to a vicinity of an inner edge side of the pair of side sheets.

The inner edge side of the side sheet constituting the first solid gather portion is preferably joined in the pair of end portions in a state of being folded back outward in the width direction of the absorbent article for pet.

The inner edge side of the side sheet constituting the second solid gather portion is preferably joined to the top surface layer in the pair of end portions.

The absorbent article for pet preferably further includes: a first high stiffness region that is formed in a vicinity of at least one of the pair of end portions and has predetermined bending stiffness; a second high stiffness region that is formed in a region, in which the absorbent core is disposed, in a central portion of the absorbent article for pet in a longitudinal direction; and a low stiffness region that is formed between the first high stiffness region and the second high stiffness region and is lower in bending stiffness than the first high stiffness region and the second high stiffness region, in which an end portion of the elastic member is positioned at the low stiffness region.

The absorbent article for pet preferably further includes a locking member that is disposed on a back surface layer side of one of the pair of end portions and configured in a rectangular shape, a longitudinal direction of which extending along the width direction of the absorbent article for pet, in which the first high stiffness region is formed in a part in which the locking member is disposed in the one of the pair of end portions.

The absorbent core preferably includes: a belt-like absorbent core main body that extends from one end side to another end side of the absorbent article for pet in the longitudinal direction; and a first extension portion that projects outwards in the width direction from a side edge on a side on which the first solid gather portion is disposed, in a central portion of the absorbent core main body in the longitudinal direction.

The absorbent article for pet preferably further includes a position mark that indicates a position used as an index during putting on the absorbent article for pet.

The position mark is preferably disposed at a position corresponding to the absorbent article main body or the first extension portion.

The position mark is preferably disposed at a position that is visually recognizable from an outer face side of the back surface layer.

Effects of the Invention

The absorbent article for pet according to the present invention can cover the back side of the pet's urinary organ appropriately by the solid gather without physically stressing the pet.

DESCRIPTION OF REFERENCE NUMERALS

Figure 1:
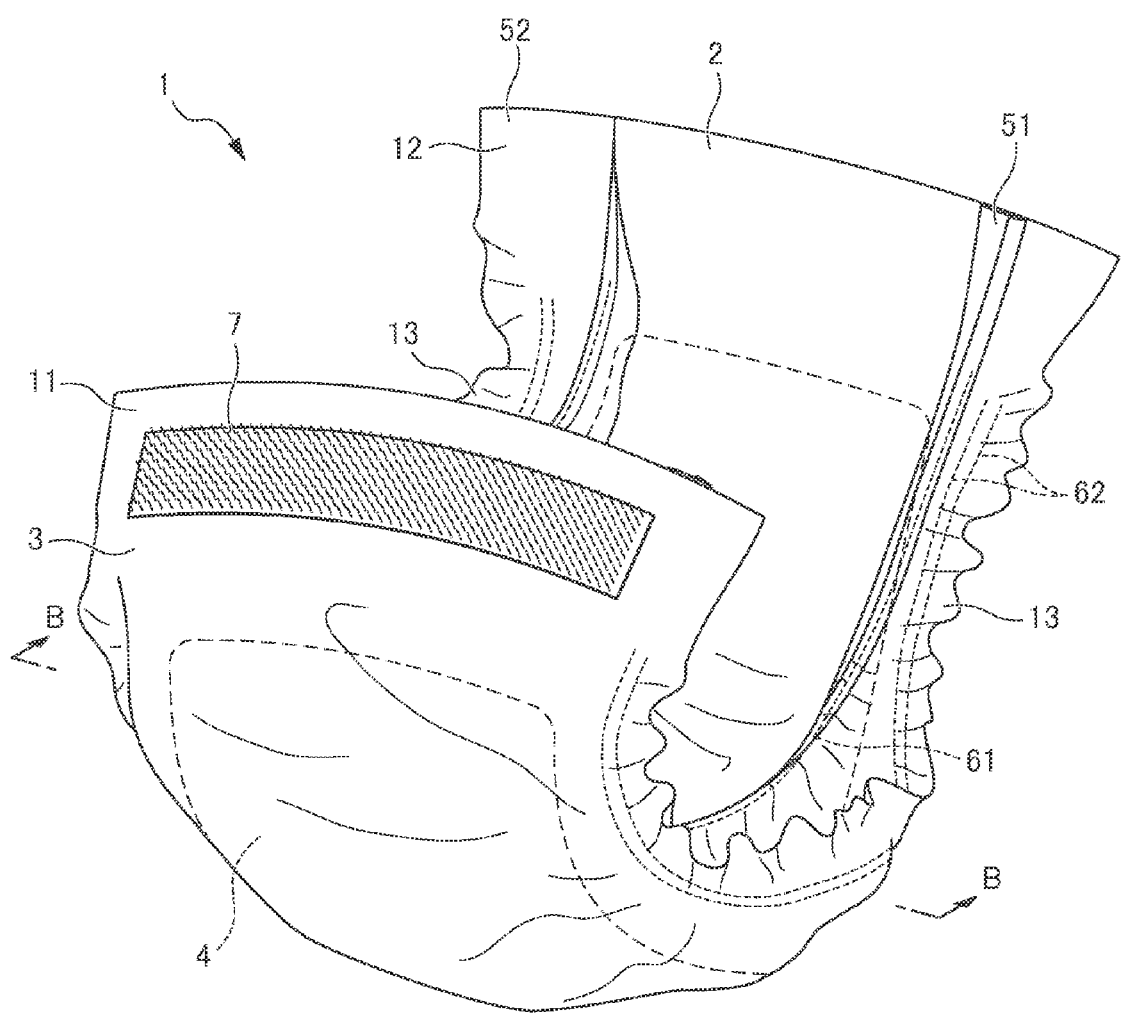
FIG. 1 is a perspective view showing an absorbent article for pet according to a first embodiment of the present invention.

1 Absorbent article for pet
2 Top sheet (Top layer)
3 Back surface layer
4 Absorbent core
7 Hook tape (Locking member)
8 Position mark
14 First solid gather portion
15 Second solid gather portion
21 First high stiffness region
22 Second high stiffness region
23 Low stiffness region
41 Absorbent core main body
42 First extension portion
51 First side sheet (Side sheet)
52 Second side sheet (Side sheet)
61 First elastic member (Elastic member)

PREFERRED MODE FOR CARRYING OUT THE INVENTION

Embodiments of the absorbent article for pet according to the present invention will be described hereinafter with reference to the drawings.

First, the absorbent article for pet according to the first embodiment will be described hereinafter with reference to FIGS. 1 to 7.

Figure 2:
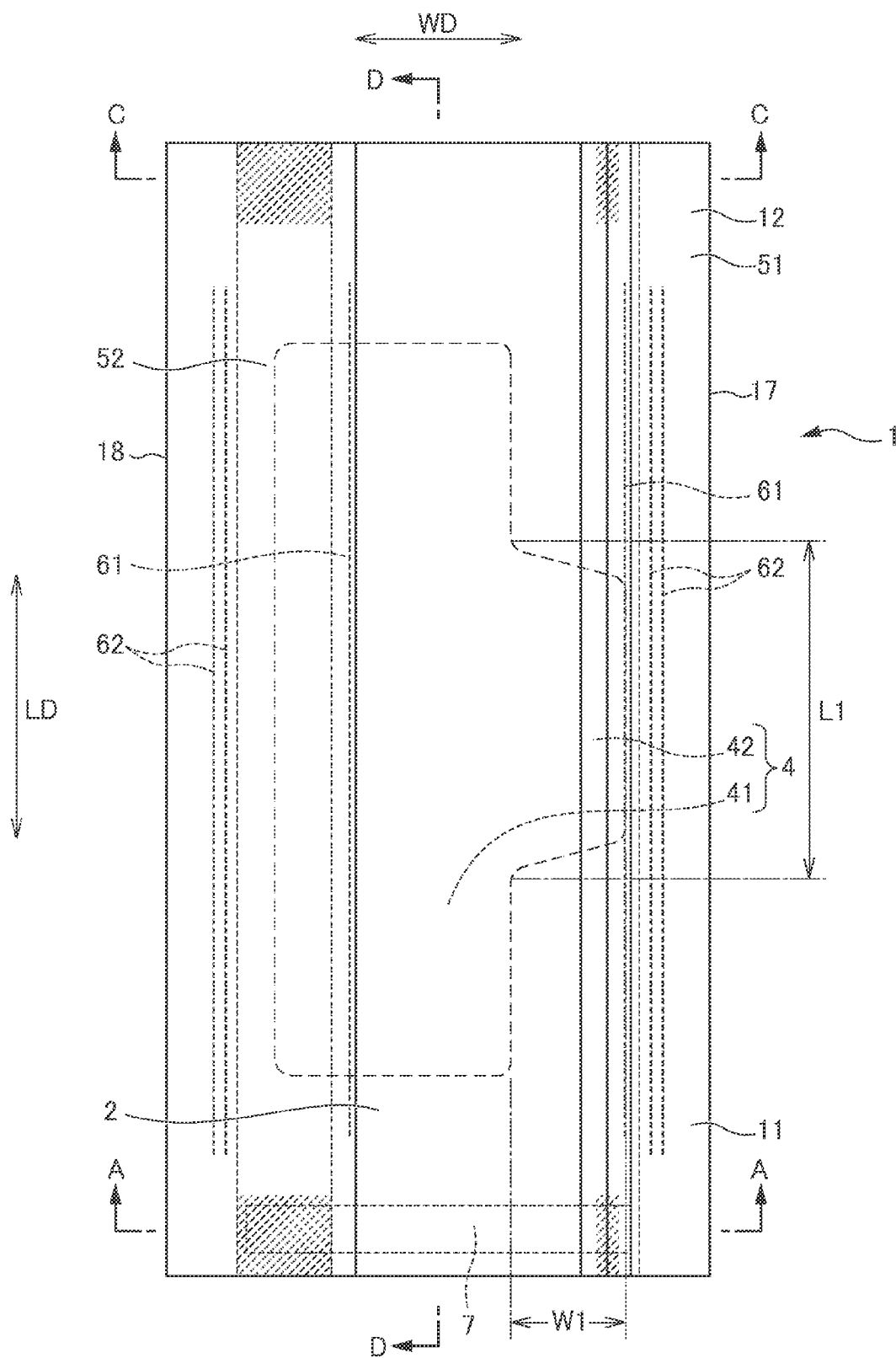
FIG. 2 is a plan view of the absorbent article for pet according to the first embodiment viewed from a top surface layer side.

As shown in FIGS. 1 and 2, an absorbent article for pet 1 according to the first embodiment is configured in a rectangular shape with a first end portion 11 and a second end portion 12 as a pair of end portions facing each other and a back side portion 17 and a front side portion 18 as a pair of side portions facing each other orthogonal to the first end portion 11 and the second end portion 12, the absorbent article for pet 1 being worn in a state of being wrapped around the pet's waist. The absorbent article for pet 1 is especially preferably used for a pet having the urethral opening located further toward the front than a position between bases of hind legs (such as miniature dachshund).

The absorbent article for pet 1 includes, as shown in FIGS. 1 to 7: a top sheet 2 constituting the liquid permeable top surface layer; a back surface sheet 31 and a waterproof sheet 32 constituting the liquid impermeable back surface layer 3; an absorbent core 4; a pair of side sheets 51, 52; a first elastic member 61 and a second elastic member 62 as the elastic member; a hook tape 7 as the locking member; and the position mark 8.

The top sheet 2 is configured in a rectangular shape. The top sheet 2 mainly constitutes a surface of a side in contact with the pet's body. As the top sheet 2, a perforated or non-perforated nonwoven fabric and a porous plastic sheet can be used. In the first embodiment, the top sheet 2 is preferably constituted of a nonwoven fabric from a viewpoint of appropriately engaging with the hook tape 7 (described later).

Figure 4:
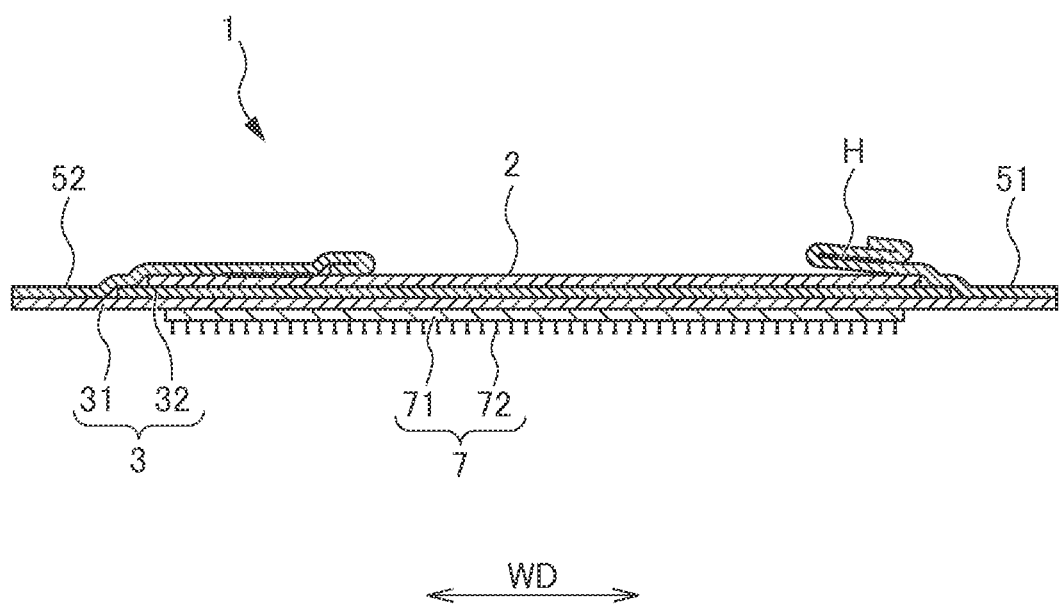
FIG. 4 is a cross-sectional view taken along the line A-A of FIG. 2.
Figure 5:
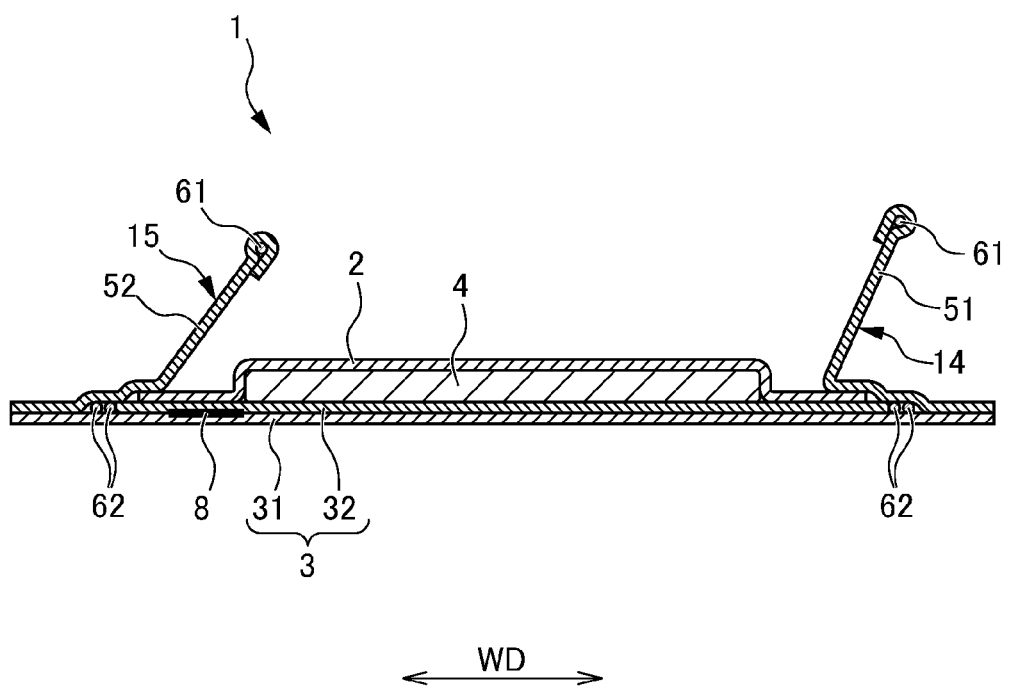
FIG. 5 is a cross-sectional view taken along the line B-B of FIG. 1.
Figure 6:
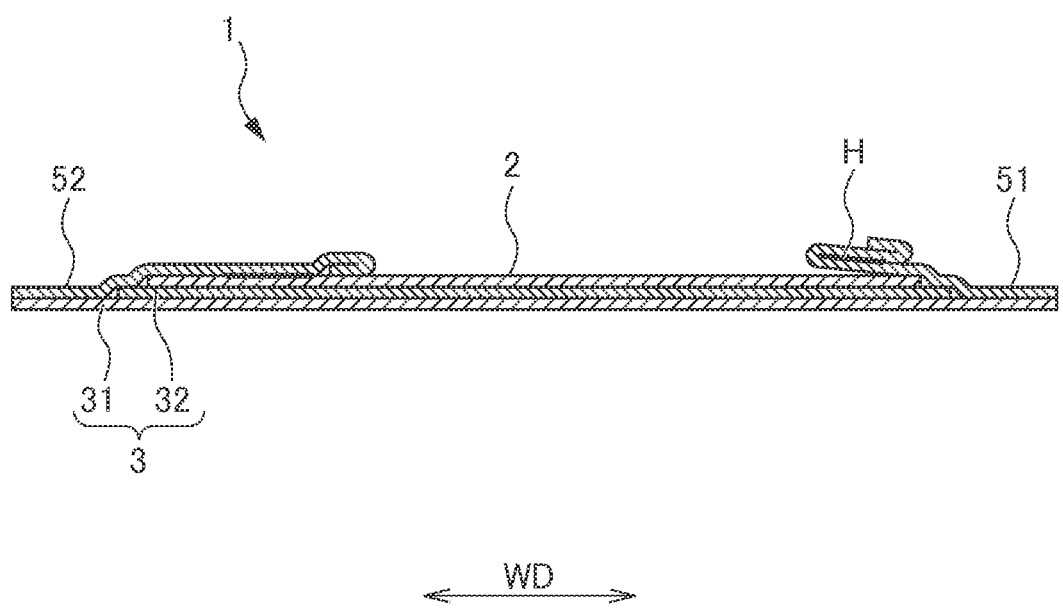
FIG. 6 is a cross-sectional view taken along the line C-C of FIG. 2.

The back surface sheet 31 is configured in a rectangular shape that is wider than, and has substantially the same length as, the top sheet 2, as shown in FIGS. 4 to 6. The back surface sheet 31 constitutes a surface of the absorbent article for pet 1, on a side not in contact with the pet's body.

The waterproof sheet 32 is configured to be smaller in width than the back surface sheet 3 and disposed on a top sheet 2 side of the back surface sheet 31.

As the back surface sheet 31 and the waterproof sheet 32, a hydrophobic nonwoven fabric, a liquid impermeable plastic film, a laminated sheet made of the nonwoven fabric and the liquid impermeable plastic film, an SMS nonwoven fabric made by sandwiching a high-water resistance melt-blown nonwoven fabric with a high-strength spun-bond nonwoven fabric, and the like can be used.

The pair of side sheets 51, 52 are configured in an elongated rectangular shape as shown in FIG. 2 and disposed on respective side portions along the longitudinal direction of a body side of the top sheet 2. The pair of side sheets 51, 52 is configured to have substantially the same length as the top sheet 2 and the back surface sheet 31. As shown in FIGS. 4 to 6, outer edges of the pair of side sheets 51, 52 correspond to side edges of the back surface sheet 31. The outer edges of the pair of side sheets 51, 52 are joined with the side edges of the back surface sheet 31.

At least a part of the inner edges of the pair of side sheets 51, 52 is a free-end, as shown in FIGS. 1 and 5. More specifically, the pair of side sheets 51, 52 includes the first side sheet 51 disposed in the back side portion 17 and the second side sheet 52 disposed in the front side portion 18. Here, the back side portion 17 is a side portion disposed on a back side of the pet's body during use of the absorbent article for pet 1; and the front side portion 18 is a side portion disposed on a front side of the pet's body during use of the absorbent article for pet 1.

As shown in FIGS. 4 to 6, the inner edge of the first side sheet 51 is not joined with the top sheet 2 in an overall length in the longitudinal direction LD of the absorbent article for pet 1. In addition, the inner edge of the first side sheet 51 is folded outward in the width direction WD of the absorbent article for pet 1, in the first end portion 11 and the second end portion 12, as shown in FIGS. 4 and 6. And then, the two-layered first side sheet 51 thus folded and layered is joined by a hotmelt adhesive H.

The inner edge of the second side sheet 52 is joined to the top sheet 2 in the first end portion 11 and the second end portion 12, by hotmelt adhesive H as shown in FIGS. 4 and 6. In addition, the inner edge of the second side sheet 52 is a free end, except for the first end portion and the second end portion in the longitudinal direction LD of the second side sheet 52, as shown in FIG. 5.

As the side sheets 51, 52, a water repellent or hydrophobic sheet is preferably used. More specifically, various nonwoven fabrics such as spun lace nonwoven fabric, spunbond nonwoven fabric, thermal bond nonwoven fabric, melt-blown nonwoven fabric, needle-punched nonwoven fabric, air-through nonwoven fabric and the like can be used. As the fiber constituting the nonwoven fabric, synthetic fiber of olefin, polyester, polyamide and the like such as polyethylene and polypropylene; regenerated fiber such as rayon and cupra; and natural fiber such as cotton can be used.

Figure 3:
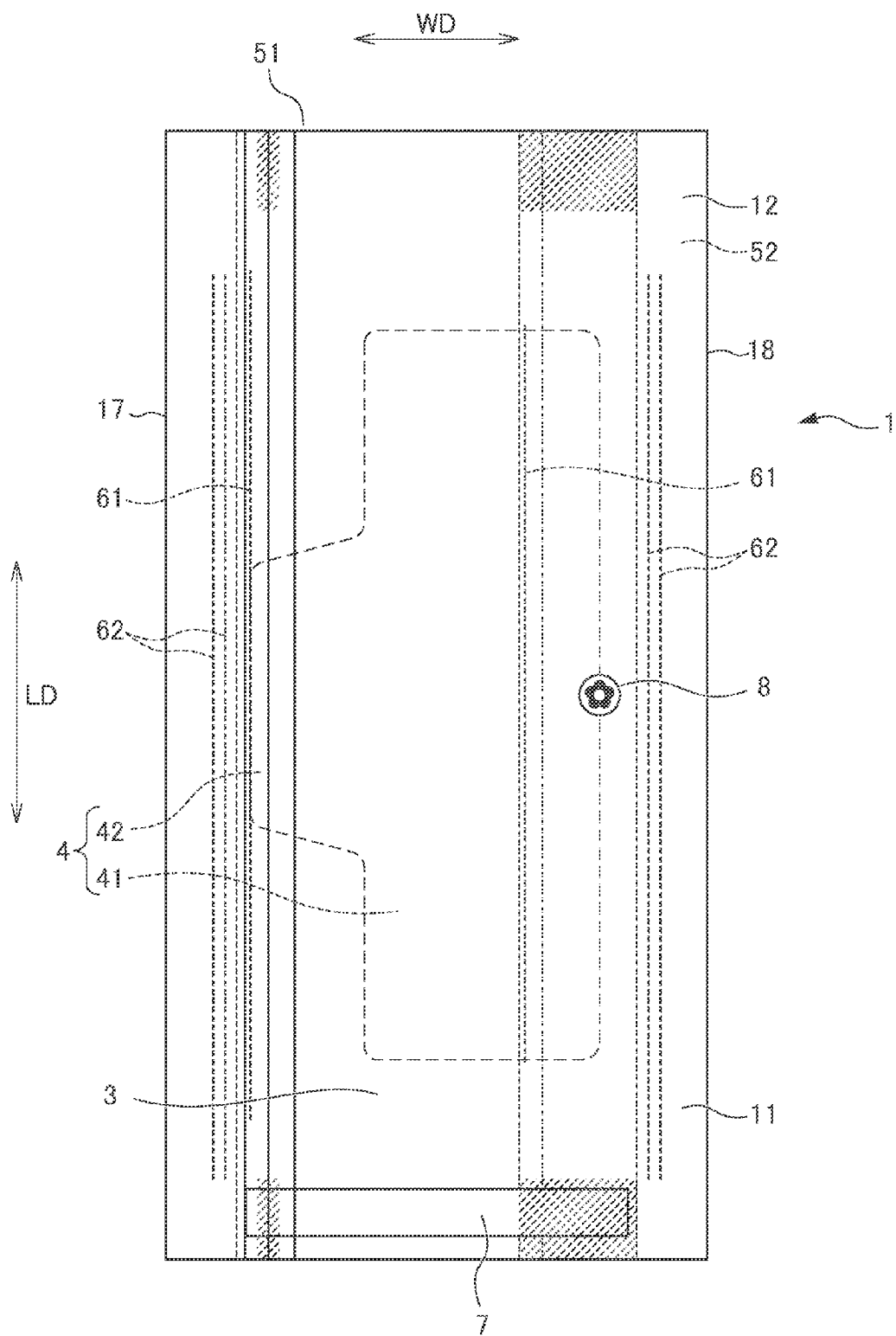
FIG. 3 is a plan view of the absorbent article for pet according to the first embodiment viewed from a back surface layer side.
Figure 7:
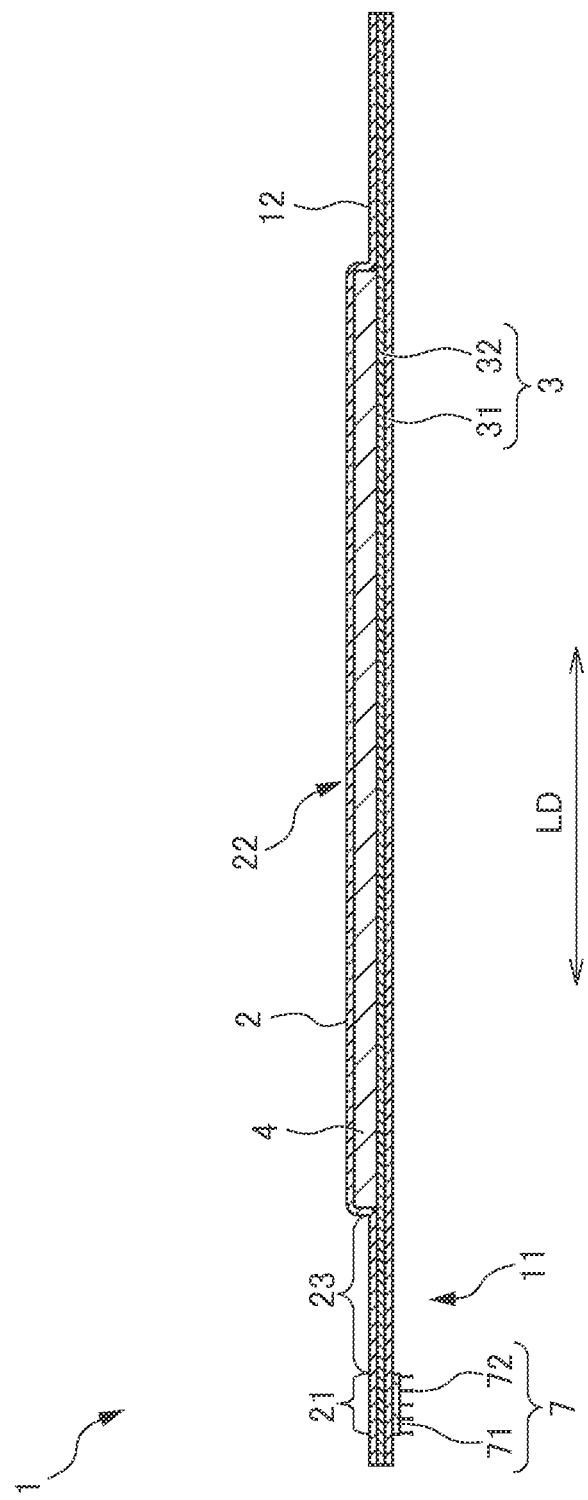
FIG. 7 is a cross-sectional view taken along the line D-D of FIG. 2.

The absorbent core 4 is disposed between the top sheet 2 and the back surface layer 3 that are layered, as shown in FIGS. 4 and 7. The absorbent core 4 includes a rectangular belt shaped absorbent core main body 41 and a first extension portion 42 that extends from the absorbent core main body 41, as shown in FIGS. 2 and 3.

The absorbent core main body 41 is disposed to extend from one end side to another end side of the absorbent article for pet 1 in the longitudinal direction LD.

The absorbent core main body 41 is configured to be smaller in length than the top sheet 2 and the back surface sheet 3, as shown in FIG. 7. The absorbent core main body 41 is not disposed in the first end portion 11 which is one end and the second end portion 12 which is another end in the longitudinal direction LD of the absorbent article for pet 1.

Width of the absorbent core main body 41 is configured to be smaller than width of the top sheet 2 and the back surface sheet. The absorbent core main body 41 is disposed disproportionately toward a side on which the second side sheet 52 is disposed (the front side portion 18 side) in the width direction WD of the absorbent article for pet 1.

The first extension portion 42 extends outward in the width direction from a central portion in the longitudinal direction of the absorbent core main body 41. More specifically, the first extension portion 42 is disposed on a side on which the first side sheet 51 is disposed, among a pair of sides along the longitudinal direction of the absorbent core main body 41. A length L1 of the first extension portion 42 in the longitudinal direction LD of the absorbent article for pet 1 is preferably 150 mm to 600 mm, or 30% to 90% of the length of the absorbent article for pet 1, from a viewpoint of appropriately covering a lower face of the urinary organ of the pet. A length W1 of the first extension portion 42 in the width direction WD of the absorbent article for pet 1 is preferably 10 mm to 100 mm, or 10% to 50% of the width of the absorbent core 4, from a viewpoint of appropriately covering a base of the urinary organ of the pet.

Figure 19:
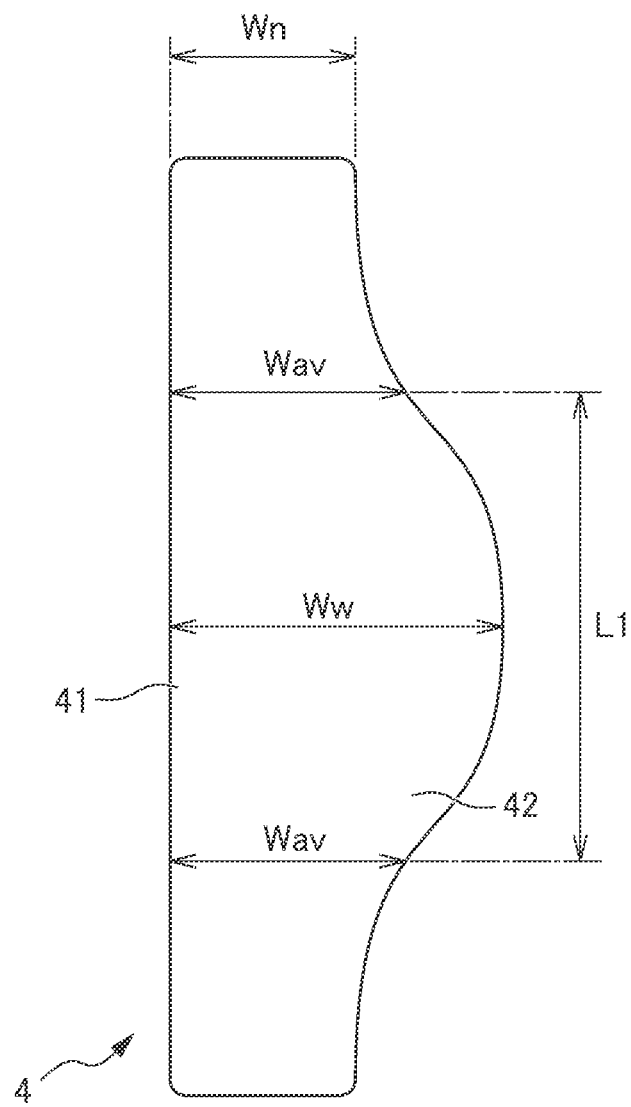
FIG. 19 is a diagram illustrating an example of a shape of the absorbent core.

In a case in which the first extension portion 42 is in a shape smoothly projecting from the absorbent article main body 41 as shown in FIG. 19, the length L1 of the first extension portion 42 in the longitudinal direction LD of the absorbent article for pet 1 is calculated as follows.

Wn is a width of the narrowest part of the absorbent core 4; Ww is a width of the widest part of the absorbent core 4; Wav is a deemed width of the extension portion obtained by averaging the width Wn and Ww (Wn+Ww/2). And then, a length between two positions having the deemed width of the extension portion Wav in the absorbent core 4 is considered to be the length L1 of the first extension portion 42 in the longitudinal direction LD of the absorbent article for pet 1.

As the absorbent core 4, fluff pulp and high absorbance polymer wrapped with a core wrapping material such as tissue can be used.

As the fluff pulp used in the absorbent core 4, chemical pulp, cellulose fiber, and artificial cellulose fiber such as rayon, acetate, and the like can be exemplified. As the high absorbance polymer, granulous or fibrous polymer of starch, acrylic acid, and amino acid can be exemplified.

The first elastic member 61 is disposed in the vicinity of the inner edge of the first side sheet 51 and the second side sheet 52, as shown in FIGS. 1 and 2. More specifically, the first elastic member 61 is sandwiched by the side sheet that is folded back from the inner edge side and fixed to the side sheet by a hotmelt adhesive (not illustrated) in an extended state as shown in FIG. 5. The first elastic member 61 is, in the extended state, greater in length than the absorbent core 4 (absorbent core main body 41) in the longitudinal direction and is disposed on the first side sheet 51 and the second side sheets 52 as shown in FIG. 2.

The second elastic member 62 is disposed in the front side portion 18 and the back side portion 17, as shown in FIGS. 1 and 2. More specifically, the second elastic member 62 is disposed between the first side sheet 51 and the second side sheet 31, and between the second side sheet 52 and the back surface sheet 31, as shown in FIG. 5. In addition, the second elastic member 62 is fixed to the side sheets 51, 52 and the back surface sheet 31 by a hotmelt adhesive in the extended state.

The second elastic member 62 is, in the extended state, greater in length than the absorbent core 4 in the longitudinal direction and is disposed in each of the front side portion 18 and the back side portion 17.

As the first elastic member 61 and the second elastic member 62, any material that is elongated and stretchable can be used, for example: natural rubber such as filiform rubber and flat rubber; thermoplastic elastomer such as urethane, ethylene-vinyl acetate copolymer (EVA), and PE. More specifically, as the thermoplastic elastomer, polybutadiene, polyisoprene, styrene-butadiene copolymer, styrene-isoprene copolymer, polyurethane, ethylene-vinyl acetate copolymer, ethylene-α-olefin copolymer and the like that are processed to be filiform or formed in a film and then slit into thin strips can be exemplified.

The hook tape 7 is disposed on an outer face of the first end portion 11 of the absorbent article for pet 1, as shown in FIGS. 1 to 3. The hook tape 7 is configured in a rectangular shape and disposed such that the longitudinal direction thereof is along the width direction WD of the absorbent article for pet 1. In addition, the hook tape 7 is attached to a position spaced apart from the side edge of the first end portion 11 by a predetermined distance.

As shown in FIG. 4, the hook tape 7 includes a belt-shaped base portion 71 and a plurality of hook portions 72 provided on one face of the base portion 71. The hook tape 7 is attached to the back surface sheet 31 such that the face on which the plurality of hook portions 72 is formed is directed outward.

The position mark 8 indicates a position used as an index during putting on the absorbent article for pet 1 on the pet. In the first embodiment, the position mark 8 is disposed on an outer side of the back surface layer 3, as shown in FIG. 3. The position mark 8 is disposed on a side on which the second side sheet 52 is disposed (the front side portion 18 side) in the width direction WD, in a central portion in the longitudinal direction LD of the absorbent article for pet 1. In the first embodiment, the position mark 8 indicates a part that should be positioned on a front side of the pet's body upon putting on the absorbent article for pet 1 on the pet.

In the first embodiment, the position mark 8 is constituted of a sticker member with a flower pattern and disposed between the waterproof sheet 32 and the back surface sheet 31 (see FIG. 5). The position mark 8 is visible from an outer side of the back surface layer 3, through the back surface sheet 31.

With the position mark 8, it is easy to understand which side portion of the belt-shaped absorbent article for pet 1 should be positioned on the front side of the pet's body, even when the absorbent article for pet 1 is viewed from the back surface layer 3 side. The position mark 8 can be constituted of a material that changes in color when the absorbent core 4 that is disposed at the position of the position mark 8 absorbs moisture.

By checking the color of the position mark 8, time to replace the absorbent article for pet 1 can be recognized appropriately.

Alternatively, the position mark 8 can be configured by printing on the outer side of the back surface layer 3.

In the above-described absorbent article for pet 1, the first elastic member 61 in the extended state is fixed to the first side sheet 51 and the second side sheet 52 along the longitudinal direction LD of the absorbent article for pet 1. In addition, the second elastic member 62 in the extended state is fixed between the side sheets 51, 52 and the back surface sheet 31, along the longitudinal direction LD of the absorbent article for pet 1.

Given this, the absorbent article for pet 1 in a natural state (without external force applied) has a solid shape as shown in FIG. 1, with the first elastic member 61 and the second elastic member 62 being contracted to thereby bring the first end portion 11 and the second end portion 12 close to each other, with the top sheet 2 side constituting an inner surface. A pair of waist gather portions 13 that are stretchable in the longitudinal direction LD are thus formed in the back side portion 17 and the front side portion 18 (see FIG. 1).

In addition, on the free end side of the first side sheet 51 and the second side sheet 52, mainly a portion, in which the first elastic member 61 is arranged, lifts. As a result, the first side sheet 51 forms the first solid gather portion 14 and the second side sheet 52 forms the second solid gather portion 15 (see FIG. 5).

Here, the length of the first solid gather portion 14 in the longitudinal direction LD of the absorbent article for pet 1 is configured to be greater than a length L1 of a first extension portion 42 in the longitudinal direction LD of the absorbent article for pet 1. More specifically, the inner edge of the first side sheet 51 constituting the first solid gather portion 14 is not joined with the top sheet 2 in an overall length in the longitudinal direction LD of the absorbent article for pet 1. In addition, the inner edge of the first side sheet 51 is folded outward in the width direction WD of the absorbent article for pet 1, and joined, in the first end portion 11 and the second end portion 12, as shown in FIGS. 4 and 6. As a result, the first solid gather portion 14 (the first side sheet 51) is constituted to be easy to lie toward the outside in the width direction WD of the absorbent article for pet 1, from a state in which the free end side thereof is upright (see FIG. 5).

On the other hand, the inner edge side of the second side sheet 52 constituting the second solid gather portion 15 is joined with the top sheet 2 in the first end portion 11 and the second end portion 12, and other parts except for the first end portion 11 and the second end portion 12 are configured to be free end. As a result, the second solid gather portion 15 (the second side sheet 52) is constituted to be easy to lie toward the inside in the width direction WD of the absorbent article for pet 1, from a state in which the free end side thereof is upright.

In addition, a central portion of the above described absorbent article for pet 1 in the longitudinal direction LD is constituted mainly of the top sheet 2, the back surface layer 3, and the absorbent core 4. The first end side 11 and the second end side 12 of the absorbent article for pet 1 are mainly constituted of the top sheet 2 and the back surface layer 3 projecting from the end edge of the absorbent core 4 (absorbent core main body 41). The hook tape 7 is disposed in the vicinity of the end edge of the first end side 11. As a result, as shown in FIG. 7, the first high stiffness region 21 having predetermined bending stiffness is formed in a part of the first end portion 11 in which the hook tape 7 is disposed, and the second high stiffness region 22 is formed in a region of the central portion of the absorbent article for pet 1 in the longitudinal direction LD in which the absorbent core 4 is disposed. In addition, a low stiffness region 23 that is lower in bending stiffness than the first high stiffness region 21 and the second high stiffness region 22 is formed between the first high stiffness region 21 and the second high stiffness region 22.

An end portion of the first elastic member 61 is positioned at the low stiffness region 23, as shown in FIGS. 1 and 2.

Figure 8:
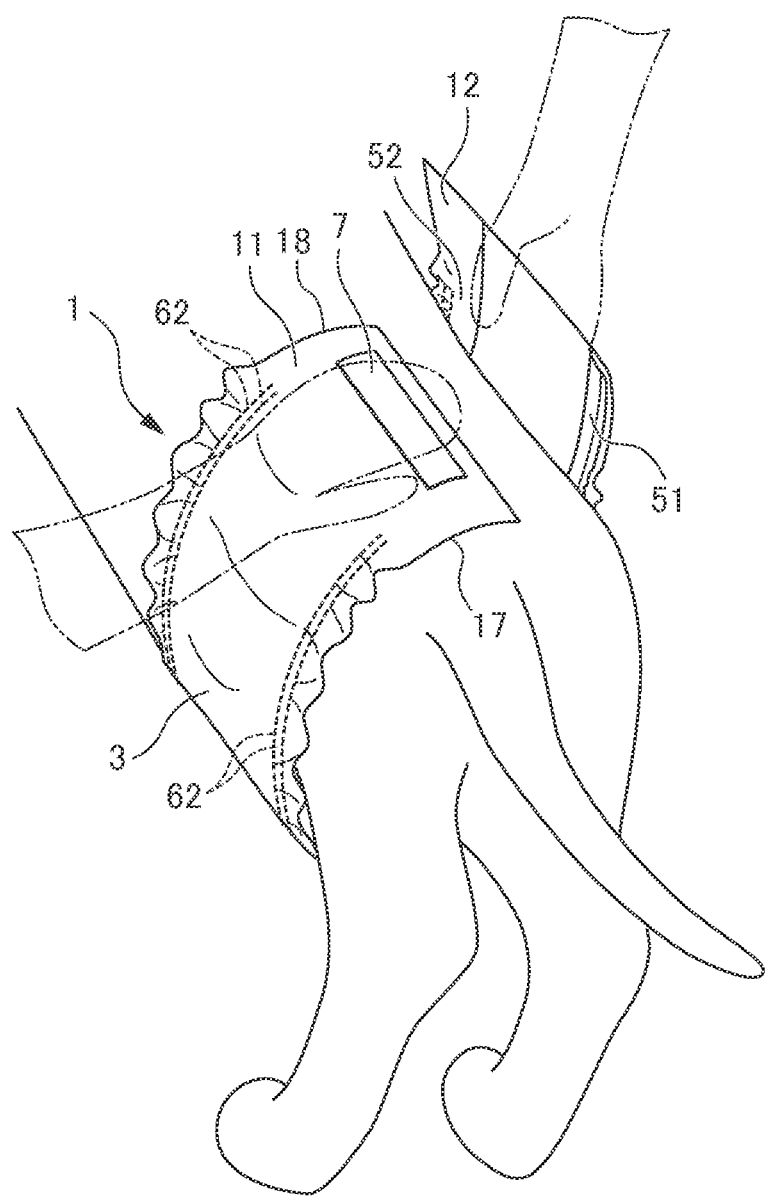
FIG. 8 is a diagram illustrating a process of putting the absorbent article for pet on a pet, in which the first end portion is placed on the pet's back.
Figure 9:
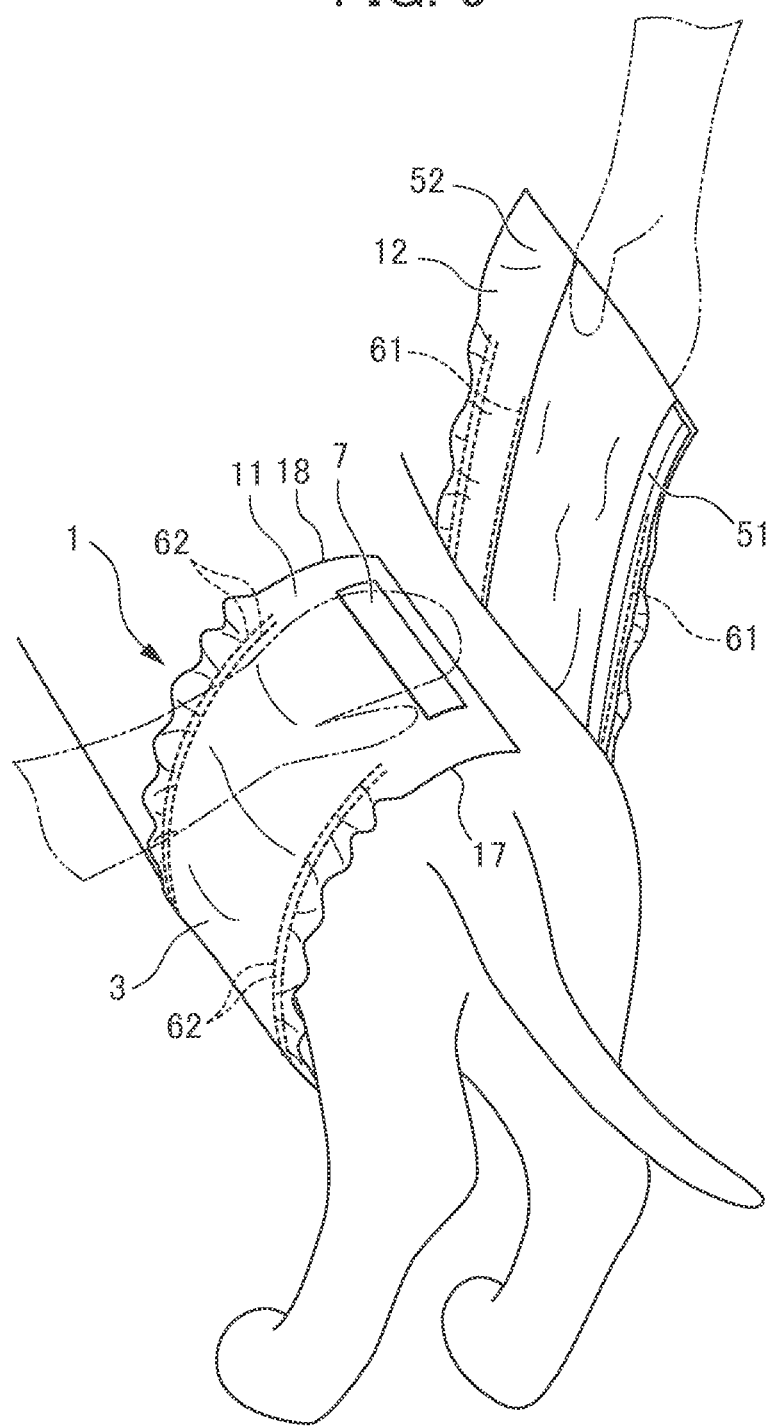
FIG. 9 is a diagram illustrating a process of putting the absorbent article for pet on a pet, in which the second end portion of the absorbent article for pet wrapped around the waist of the pet is pulled to bring the absorbent article for pet into close contact with the waist of the pet.
Figure 10:
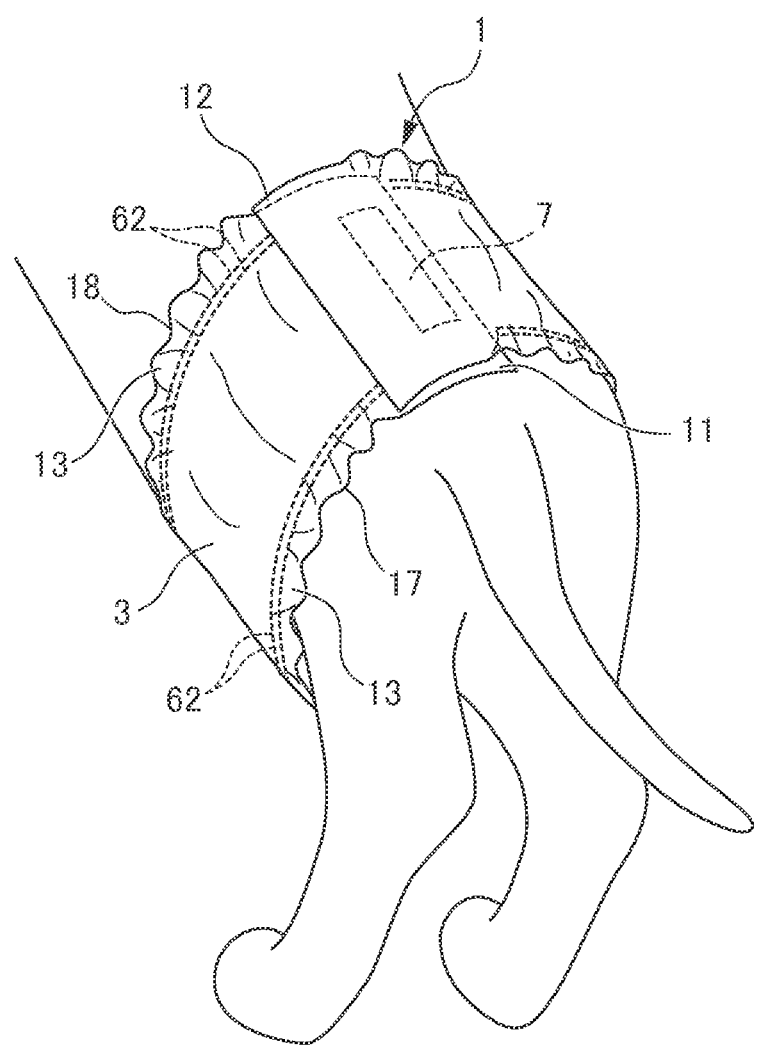
FIG. 10 is a diagram illustrating a state in which the absorbent article for pet is put around the pet's waist.
Figure 11:
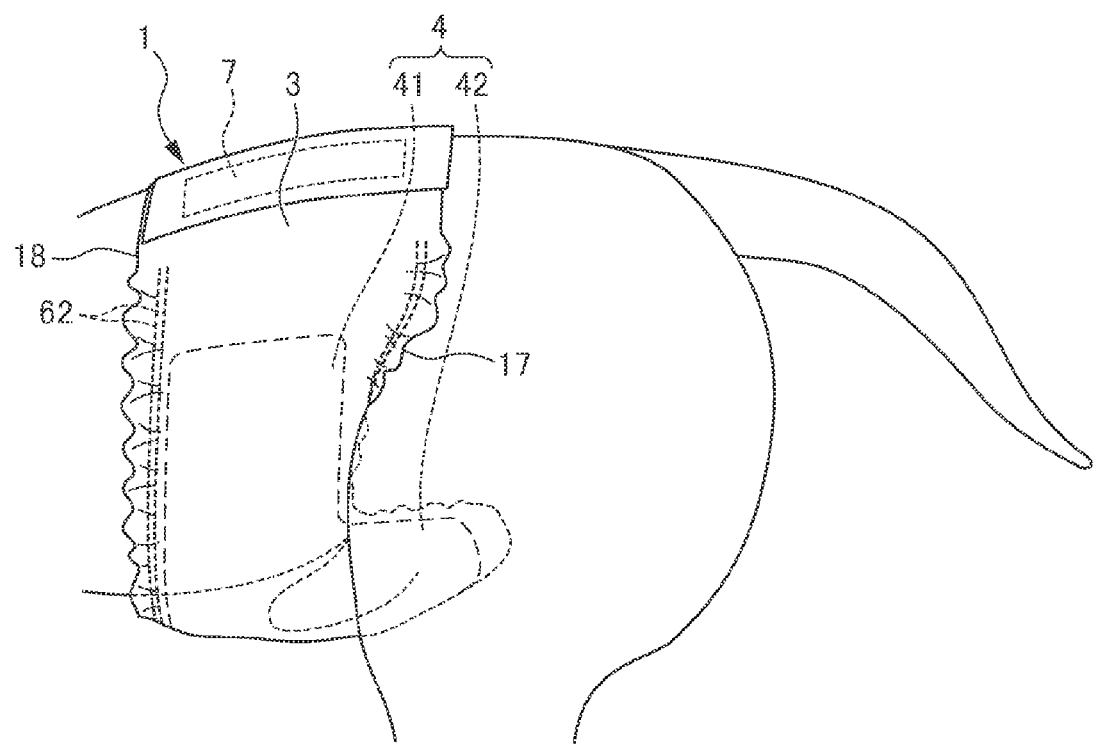
FIG. 11 is a diagram illustrating a state in which the absorbent article for pet is put around the pet's waist, viewed from a left side of the pet.

Next, steps of putting on the absorbent article for pet 1 according to the first embodiment will be described hereinafter with reference to FIGS. 8 to 11. FIGS. 8 to 11 are diagrams illustrating a process of putting the absorbent article for pet 1 on a pet: FIG. 8 is a diagram illustrating a state in which the first end portion 11 is placed on the pet's back; FIG. 9 is a diagram illustrating a process of putting the absorbent article for pet 1 on a pet, in which the second end portion 12 of the absorbent article for pet 1 wrapped around the waist of the pet is pulled to bring the absorbent article for pet 1 into close contact with the waist of the pet; FIG. 10 is a diagram illustrating a state in which the absorbent article for pet 1 is put around the pet's waist; and FIG. 11 is a diagram illustrating a state in which the absorbent article for pet 1 is put around the pet's waist, viewed from a left side of the pet.

First, as shown in FIG. 8, the first end portion 11 of the absorbent article for pet 1 is placed on the back of the pet and the vicinity of the first end portion 11 is held by one hand of a user. Here, a side on which the position mark 8 is provided is placed on the front side of the pet's body, based on the position mark 8 disposed on the back surface layer 3 side. In this state, the first high stiffness region 21 is folded back from the low stiffness region 23, as a starting point for folding, at which the end portion of the first elastic member 61 is positioned, toward the back surface layer 3 (not illustrated). By folding back the first high stiffness region 21, an outward force in the width direction WD is applied to the first solid gather portion 14, which is made upright by a stretching force of the first elastic member 61, thereby making the first solid gather portion 14 lie outward.

Thereafter, in a state in which the first end portion 11 is held by one hand, the second end portion 12 of the absorbent article for pet 1 is held by the other hand and wrapped around the pet's body to cover the abdomen of the pet.

Next, as shown in FIG. 9, the second end portion 12 is pulled upward and the pair of waist gather portions 13 is brought into close contact with the pet's waist; and then, as shown in FIG. 10, the inside of the second end portion 12 is engaged with the hook tape 7 provided on the outer face of the first end portion 11. The absorbent article for pet 1 is thus wrapped around the pet's waist in a state in which the first solid gather portion 14 lies outward.

In the abovementioned process, upon putting the absorbent article for pet 1 on the pet, the absorbent article for pet 1 is brought close to the hind leg side of the pet's body and wrapped around the pet's body, so as to cover the entire urinary organ of the pet by the absorbent core 4. In the first embodiment, the absorbent core main body 41 is disposed disproportionately to the side on which the second side sheet 52 is disposed (the front side of the pet's body) in the width direction WD of the absorbent article for pet 1. In addition, the first extension portion 42 extends outward in the width direction WD of the absorbent article for pet 1 (to the back side of the pet's body). The first extension portion 42 can thus be disposed to cover a lower portion of the base of the pet's urinary organ, positioned between the hind legs, as shown in FIG. 11. In addition, the absorbent core main body 41 is not provided in a part of the absorbent article for pet 1 disposed close to the pet's hind legs. In addition, since the absorbent core 4 (the absorbent core main body 41) does not interfere with the pet's hind legs when the absorbent article for pet 1 is wrapped around the pet's body, the absorbent article for pet 1 can be appropriately wrapped around the pet's body at a position close to the hind legs.

The above-described absorbent article for pet 1 according to the first embodiment provides the following operation and effects.

(1) The first solid gather portion 14 is configured to be easier to lie outward in the width direction WD of the absorbent article for pet 1. Therefore, when the absorbent article for pet 1 is wrapped around the pet's body, the first solid gather portion 14 (the first side sheet 51) in a state of lying outward can be arranged to appropriately cover the lower part and back part of the base of the pet's urinary organ. As a result, the absorbent article for pet 1 can be put on without applying an intense stress to the base of the pet's urinary organ and the pet will not be physically stressed.

(2) The first solid gather portion 14 and the second solid gather portion 15 are respectively configured including the side sheets 51, 52 and the first elastic member 61. The first solid gather portion 14 and the second solid gather portion 15 can thus be appropriately upright from the top sheet 2.

(3) The inner edge of the first side sheet 51 constituting the first solid gather portion 14 is joined in the first end portion 11 and the second end portion 12 of the absorbent article for pet 1, in a state of being folded outward in the width direction WD of the absorbent article for pet 1. The inner edge of the first side sheet 51, which is an upright edge of the first solid gather portion 14, can thus be fixed in a state of being directed outward in the width direction WD of the absorbent article for pet 1, in the first end portion 11 and the second end portion 12. As a result, the first solid gather portion 14 can be made easier to lie outward in the width direction WD of the absorbent article for pet 1.

(4) The inner edge of the second side sheet 52 constituting the second solid gather portion 15 is joined to the top sheet 2 in the first end portion 11 and the second end portion 12 of the absorbent article for pet 1. The inner edge of the second side sheet 52, which is an upright edge of the second solid gather portion 15, can thus be fixed in a state of being directed inward in the width direction WD of the absorbent article for pet 1, in the first end portion 11 and the second end portion 12. Since the second solid gather portion 15 can be made easy to lie inward in the width direction of the absorbent article for pet 1, leakage of urine from the front side of the pet's body can be effectively prevented.

In a case in which the absorbent article for pet 1 is put on to a male pet, a top of the sex organ extending to the front side of the body can be appropriately covered by the second solid gather portion 15 that can easily lie inward. Therefore, leakage of urine from the front side of the pet's body can be prevented more effectively. In addition, since the top of the sex organ is in contact with the second solid gather portion 15, the dislocation of the absorbent article for pet 1 to the back side of the body can be prevented.

(5) The absorbent article for pet 1 is configured to include: the first high stiffness region 21 disposed in the first end portion 11; the second high stiffness region 22 disposed in the central portion in the longitudinal direction LD; and the low stiffness region 23 disposed between the first high stiffness region 21 and the second high stiffness region 22, and the end portion of the first elastic member 61 is positioned at the low stiffness region 23. As a result, the first high stiffness region 21 can be easily folded back from the low stiffness region 23, as a starting point for folding, at which the end portion of the first elastic member 61 is positioned, toward the back surface layer 3. By folding back the first high stiffness region 21, an outward force can be applied to the first solid gather portion 14, which is made upright by a stretching force of the first elastic member 61, thereby making the first solid gather portion 14 easier to lie outward.

(6) The first high stiffness region 21 is configured to include the hook tape 7. The high stiffness region 21 can thus be easily obtained by using a member for making the first end portion 11 engaged with the second end portion 12. Since no dedicated member is employed for forming the high stiffness region 21, the manufacturing cost of the absorbent article for pet 1 can be reduced.

(7) The absorbent core main body 41 is disposed disproportionately to the side on which the second side sheet 52 is disposed (the front side of the pet's body) in the width direction WD of the absorbent article for pet 1, and the first extension portion 42 is provided extending outward in the width direction WD of the absorbent article for pet 1. The first extension portion 42 can thus be disposed to cover a lower portion of the base of the pet's urinary organ, positioned between the hind legs. In addition, the absorbent core main body 41 is not provided in a part of the absorbent article for pet 1 disposed close to the pet's hind legs. In addition, since the absorbent core 4 (the absorbent core main body 41) does not interfere with the pet's hind legs when the absorbent article for pet 1 is wrapped around the pet's body, the absorbent article for pet 1 can be appropriately wrapped around the pet's body at a position close to the hind legs. In other words, in the absorbent article for pet that is used in a state of being wrapped around the pet's waist, the absorbent core 4 can appropriately cover the entire urinary organ.

(8) The absorbent core main body 41 is disposed to extend from a first end side to a second end side in the longitudinal direction LD of the absorbent article for pet 1. As a result, when the absorbent article for pet 1 is put on to the pet, the absorbent core main body 41 can be arranged also in side portions of the pet's body, except for a part between the hind legs in which the first extension portion 42 is provided. Therefore, even if the pet urinates while lying down, urine can be appropriately absorbed by the absorbent core main body 41 disposed on the side portions of the pet's body.

(9) The position mark 8 indicating a part that should be positioned on the front side of the pet's body is provided at a position visible from the outside of the back surface layer 3. It is thus easy to understand which side portion of the belt-shaped absorbent article for pet 1 should be positioned on the front side of the pet's body, even when the absorbent article for pet 1 is viewed from the back surface layer 3 side.

Figure 12:
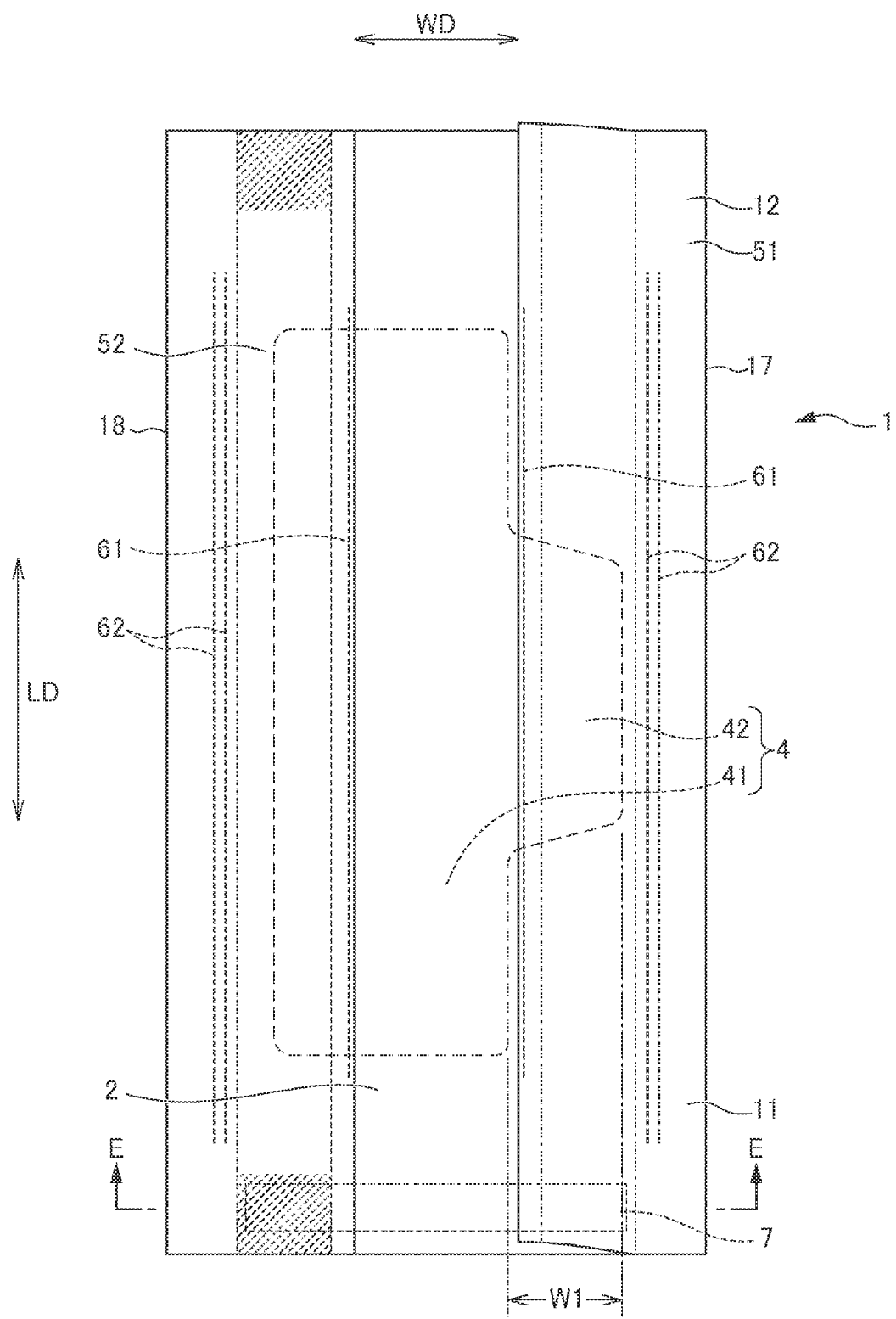
FIG. 12 is a plan view of the absorbent article for pet according to the second embodiment viewed from the top surface layer side.
Figure 13:
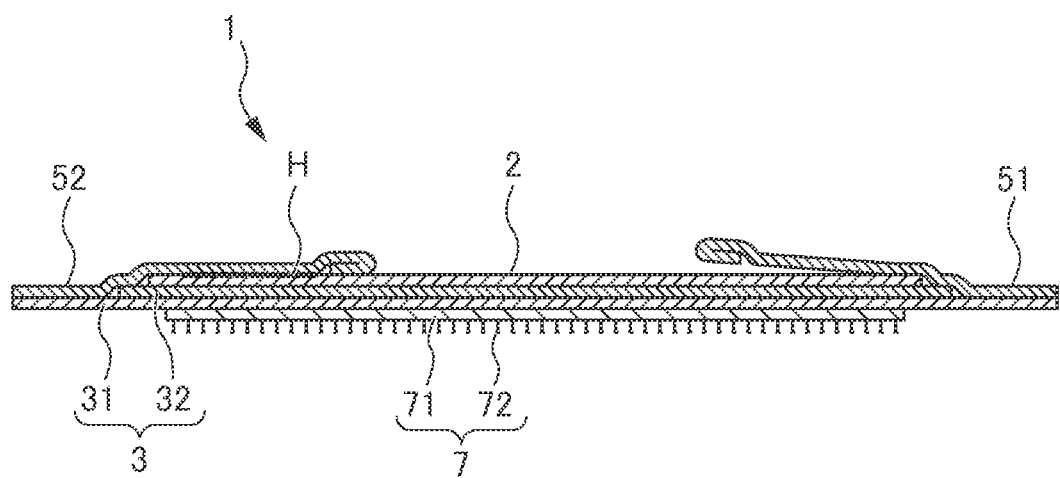
FIG. 13 is a sectional view taken along the line E-E of FIG. 12.

The absorbent article for pet 1 according to the second embodiment will be described hereinafter with reference to FIGS. 12 and 13. FIG. 12 is a plan view of the absorbent article for pet 1 according to the second embodiment. FIG. 13 is a cross-sectional view taken along the line E-E of FIG. 12.

In the description of the following embodiments, the same constituent features are referred by the same reference numerals and description thereof is omitted or simplified.

The absorbent article for pet 1 according to the second embodiment is different from the first embodiment mainly in the configuration of the first solid gather portion 14.

In the second embodiment, as shown in FIGS. 12 and 13, the inner edge of the rear side sheet 51 is a free end over an entire length in the longitudinal direction. In addition, the inner edge of the first side sheet 51 is not folded outward in the width direction WD of the absorbent article for pet 1 in the first end portion 11 and the second end portion 12.

The absorbent article for pet 1 according to the second embodiment provides the above effects (1), (2) and (4) to (9).

Figure 14:
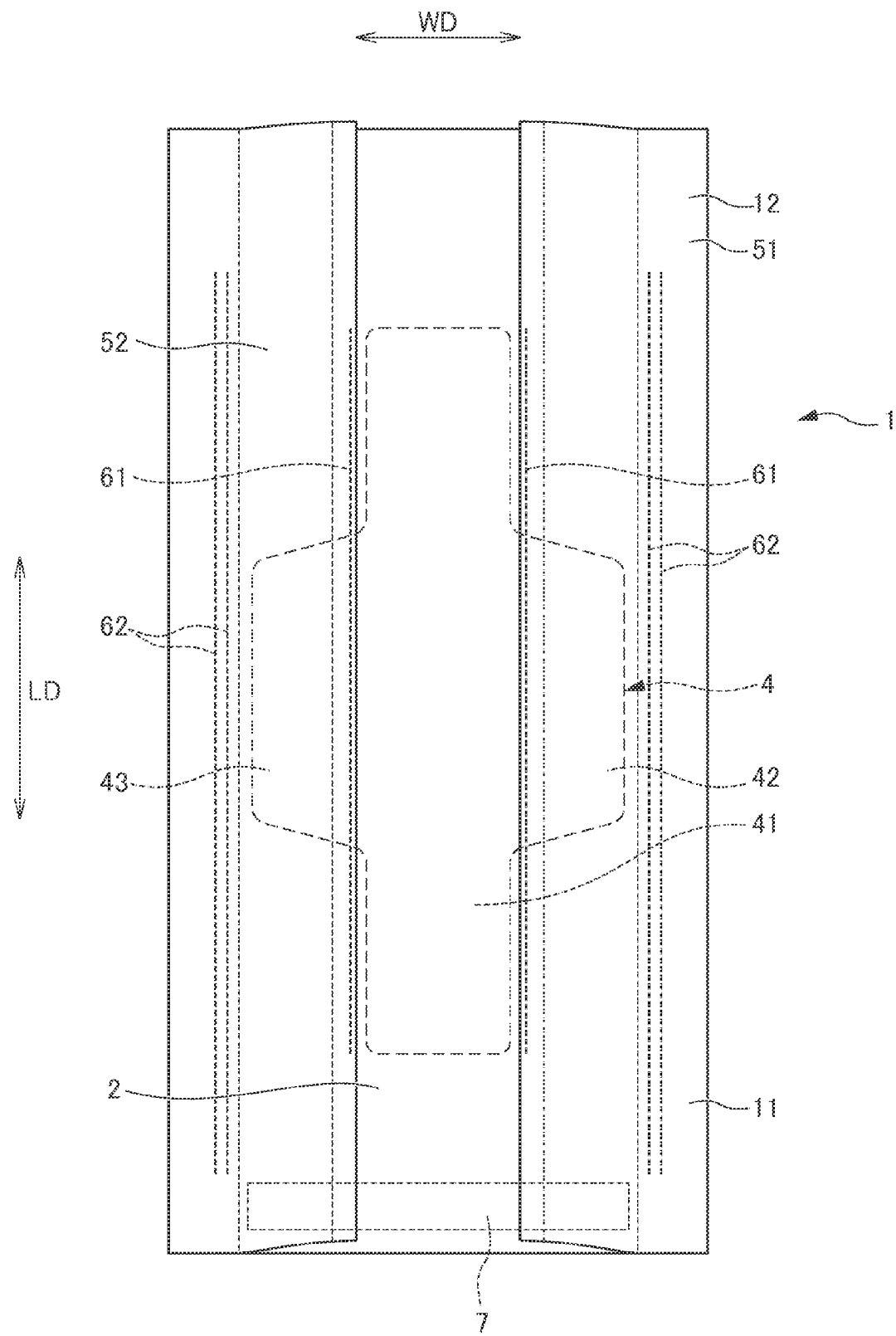
FIG. 14 is a plan view of the absorbent article for pet according to the third embodiment viewed from the top surface layer side.

The absorbent article for pet 1 according to the third embodiment will be described hereinafter with reference to FIG. 14. FIG. 14 is a plan view of the absorbent article for pet 1 according to the third embodiment.

The absorbent article for pet 1 according to the third embodiment is different from the first embodiment mainly in the configuration of the absorbent core 4.

As shown in FIG. 14, the absorbent core 4 in the third embodiment further includes a second extension portion 43 that extends outward in the width direction from a side on which the second side sheet 52 is disposed, among the pair of side portions of the absorbent core main body 41. In the third embodiment, the width of the absorbent article main body 41 is configured to be smaller than in the first embodiment.

The second extension portion 43 is disposed in a central portion in the longitudinal direction of the absorbent core main body 41. The second extension portion 43 is configured in the same shape and same size as the first extension portion 42.

In the third embodiment, as shown in FIG. 14, the inner edge of the first side sheet 51 and the inner edge of the second side sheet 52 are free ends over an entire length in the longitudinal direction. In addition, the inner edge of the first side sheet 51 and the inner edge of the second side sheet 52 are not folded outward in the width direction WD of the absorbent article for pet 1 in the first end portion 11 and the second end portion 12.

The absorbent article for pet 1 according to the third embodiment provides the following effects, in addition to the above effects (1), (2) and (4) to (9).

(10) The absorbent core 4 is configured including the second extension portion 43 that extends outward in the width direction from a side on which the second side sheet 52 is disposed, among the pair of side portions of the absorbent core main body 41. The absorbent core 4 can thus be configured to be symmetrical about a central line extending in the longitudinal direction LD of the absorbent article for pet 1. As a result, the absorbent core 4 can appropriately cover the entire urinary organ regardless of a direction of putting the absorbent article for pet 1 on the pet.

In addition, as the absorbent core 4 can thus be configured to be symmetrical about a central line extending in the longitudinal direction LD of the absorbent article for pet 1, meandering of a conveyance line can be reduced in the manufacturing process of the absorbent article for pet 1. The absorbent article for pet 1 can thus be manufactured efficiently.

The preferred embodiments of the present invention have been described; however, the present invention is not limited thereto and can be modified accordingly.

For example, the position mark 8 is disposed on the back surface layer 3 side in the first embodiment; however, the present invention is not limited thereto. In other words, the position mark can also be disposed on the top sheet side.

Figure 15:
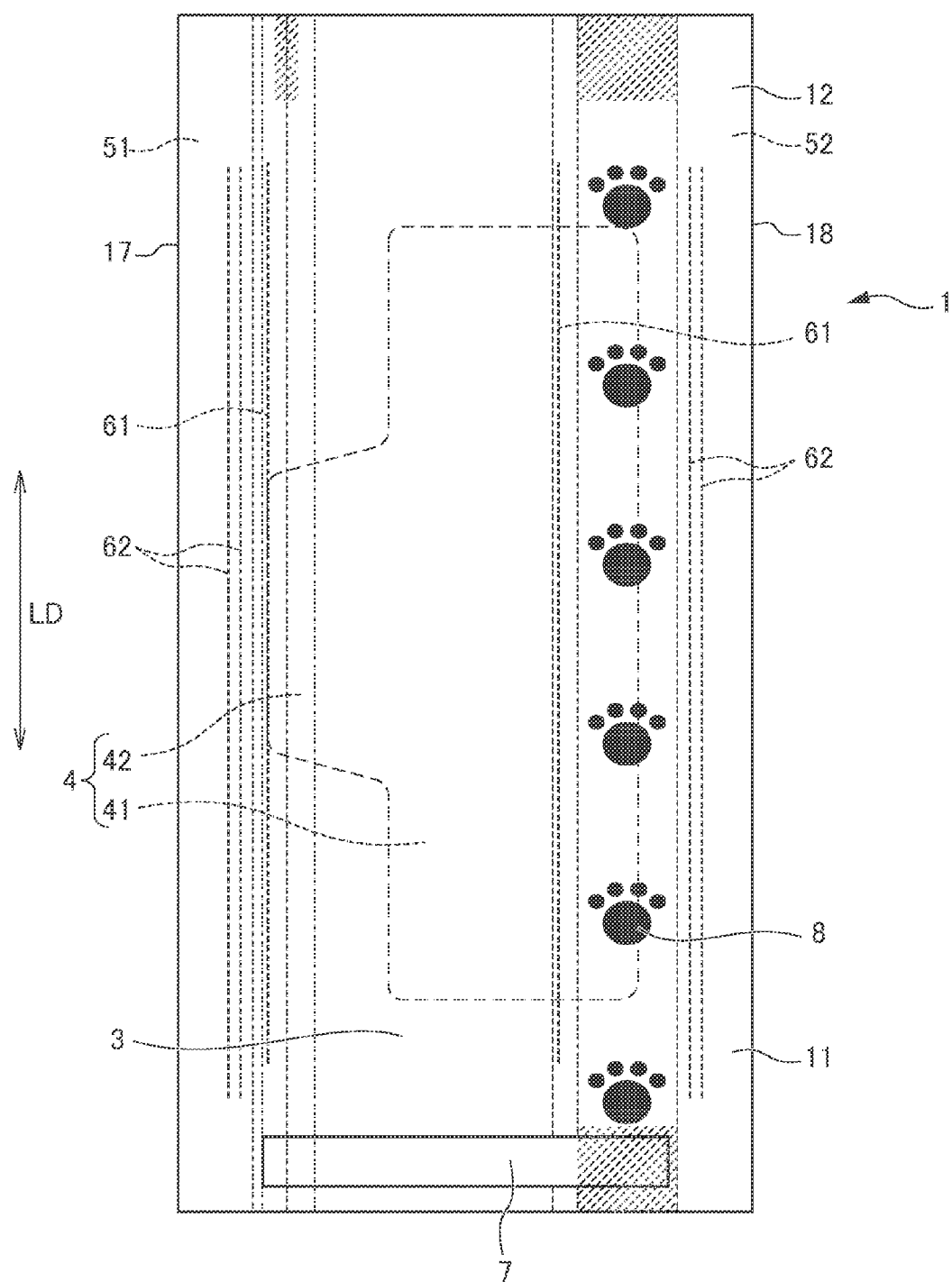
FIG. 15 is a diagram illustrating an example of arrangement of a position mark.

In addition, in the first embodiment, the position mark 8 is disposed on a side on which the second side sheet 52 is disposed in the width direction WD, in a central portion in the longitudinal direction LD of the absorbent article for pet 1; however, the present invention is not limited thereto. In other words, a plurality of position marks 8 can be provided at predetermined intervals in the longitudinal direction LD, as shown in FIG. 15.

Figure 16A:
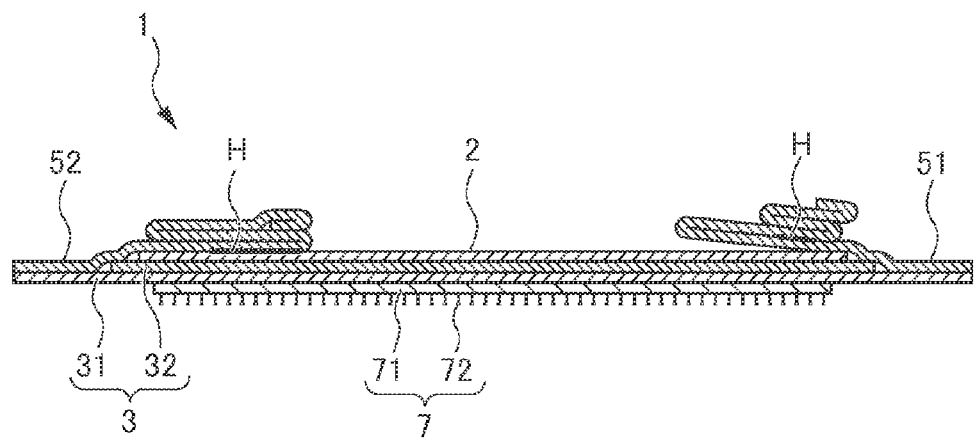
FIG. 16A is a diagram illustrating a first modification of the solid gather portion, corresponding to the cross-sectional view taken along the line A-A of FIG. 2.
Figure 16B:
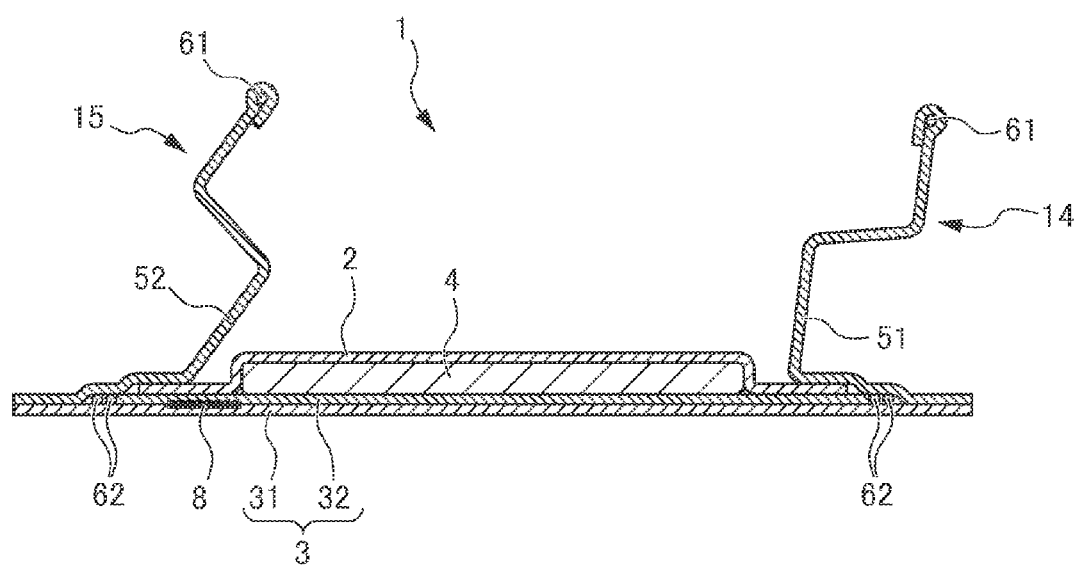
FIG. 16B is a diagram illustrating the first modification of the solid gather portion, corresponding to the cross-sectional view taken along the line B-B of FIG. 1.
Figure 17A:
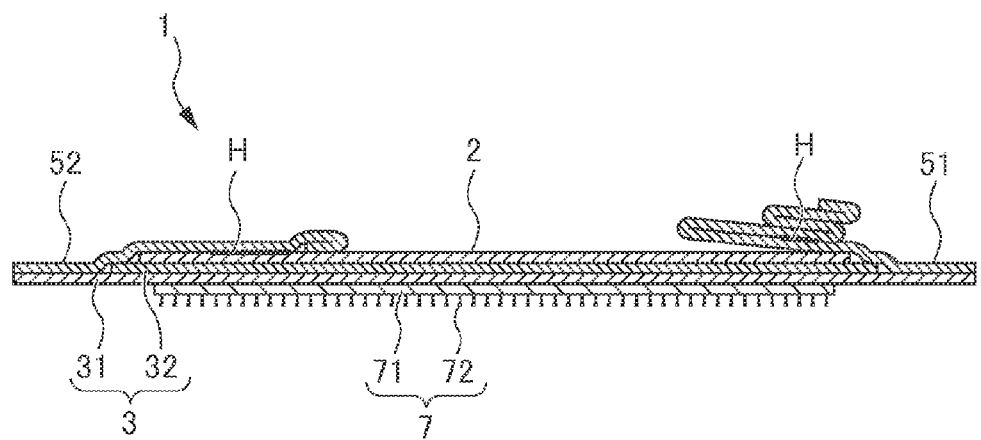
FIG. 17A is a diagram illustrating a second modification of the solid gather portion, corresponding to the cross-sectional view taken along the line A-A of FIG. 2.
Figure 17B:
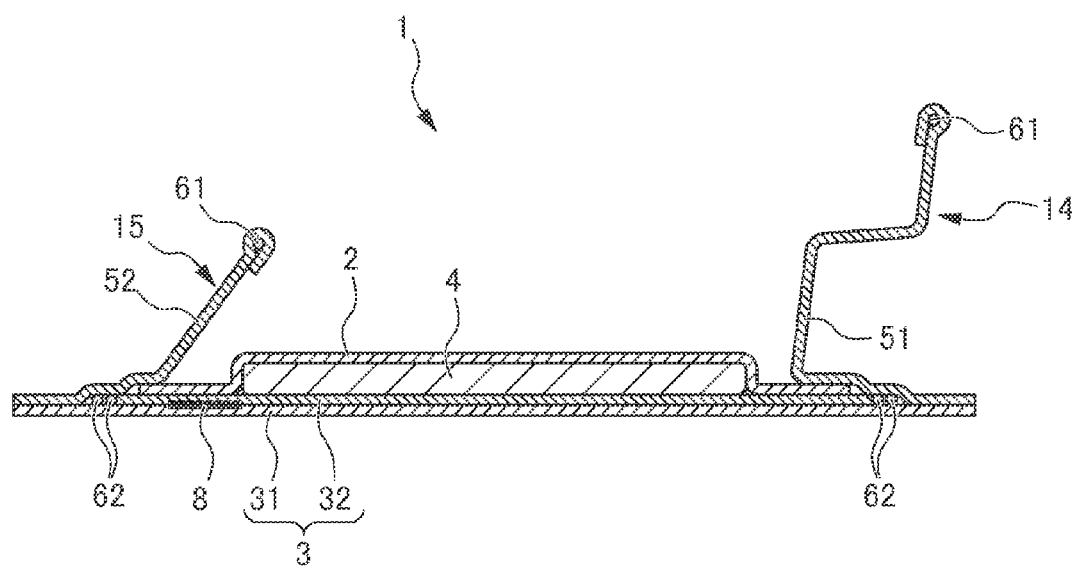
FIG. 17B is a diagram illustrating the second modification of the solid gather portion, corresponding to the cross-sectional view taken along the line B-B of FIG. 1.
Figure 18A:
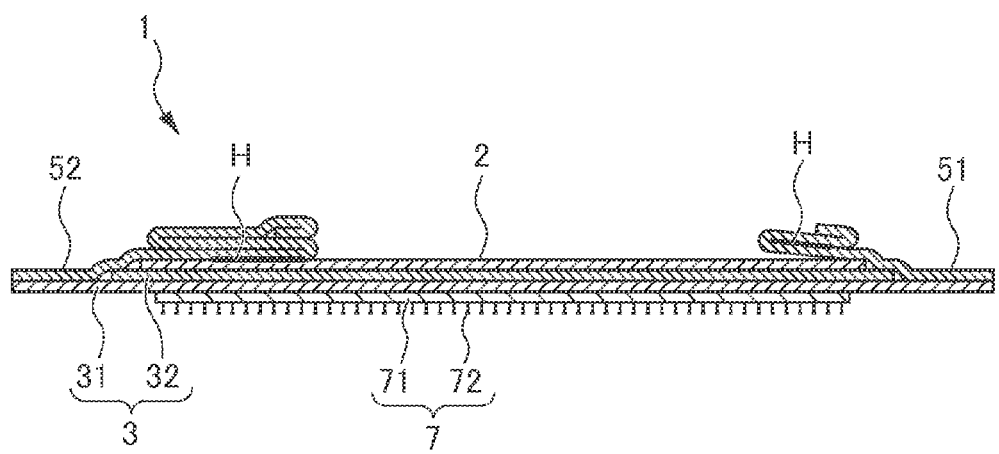
FIG. 18A is a diagram illustrating a third modification of the solid gather portion, corresponding to the cross-sectional view taken along the line A-A of FIG. 2.
Figure 18B:
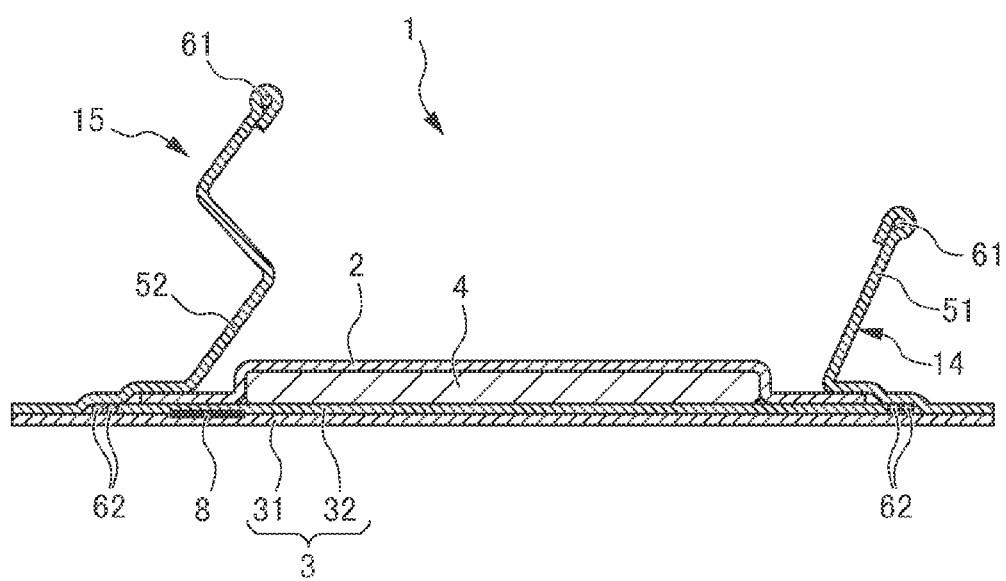
FIG. 18B is a diagram illustrating the third modification of the solid gather portion, corresponding to the cross-sectional view taken along the line B-B of FIG. 1.

Furthermore, in the first to third embodiments, the first solid gather portion 14 and the second solid gather portion 15 are respectively configured without folding the side sheet; however, the present invention is not limited thereto. In other words, as shown in FIGS. 16A and 16B, the first solid gather portion 14 and the second solid gather portion 15 can be configured by folding the first side sheet 51 and the second side sheet 52 for multiple times (for example, twice). Alternatively, as shown in FIGS. 17A and 17B, the first solid gather portion 14 can be configured by folding the first side sheet 51 for multiple times, while the second solid gather portion 15 is configured without folding the second side sheet 52. Yet alternatively, as shown in FIGS. 18A and 18B, the first solid gather portion 14 can be configured without folding the first side sheet 51, while the second solid gather portion 15 is configured by folding the second side sheet 52 for multiple times.

By configuring the solid gather portions by folding the side sheets for multiple times, the upright height of the solid gather portions can be increased.

Furthermore, in the first to third embodiments, the back surface layer 3 is composed of two layers: the back surface sheet 31 and the waterproof sheet 32; however, the present invention is not limited thereto. In other words, the back surface layer can also be constituted only of the back surface sheet or the waterproof sheet.

The invention claimed is:

1. An absorbent article for a pet comprising:
    a liquid permeable top surface layer;
    a liquid impermeable back surface layer;
    an absorbent core disposed between the top surface layer and the back surface layer,
    a pair of end portions of the absorbent article for the pet, each of the pair of end portions facing each other;
    a pair of side portions, each of the pair of side portions facing each other and orthogonal to the pair of end portions,
    a first solid gather portion disposed on a top surface layer side of one of the pair of side portions, the first solid gather portion rising up from the top surface layer,
    a second solid gather portion disposed on the top surface layer side of the other of the pair of side portions, the second solid gather portion rising up from the top surface layer,
    wherein the absorbent article for the pet has a rectangular shape, and is configured to be worn in a state of being wrapped around a waist of the pet,
    wherein the first solid gather portion is configured to easily lie outward in a width direction of the absorbent article for the pet, wherein
    the first solid gather portion and the second solid gather portion each include:
        a pair of side sheets, each of the pair of side sheets being respectively disposed on the top surface layer side of each of the pair of side portions, an outer edge of each of the pair of side sheets is joined with the top surface layer or the back surface layer and at least a part of an inner edge of the pair of side sheets is a free end; and
        an elastic member that is attached to a vicinity of an inner edge side of each of the pair of side sheets, and
    the inner edge side of the side sheet constituting the first solid gather portion is folded back outward in the width direction of the absorbent article for the pet onto an outer surface of the side sheet constituting the first gather portion and joined to the outer surface of the side sheet constituting the first gather portion in the pair of end portions by a hot melt adhesive and not joined to the top surface layer, and
    the inner edge side of the side sheet constituting the second solid gather portion is joined to the top surface layer of the pair of end portions.

2. The absorbent article for a pet according to claim 1, further comprising:
    a first high stiffness region that is formed in a vicinity of at least one of the pair of end portions and has a predetermined bending stiffness;
    a second high stiffness region that is formed in a region, in which the absorbent core is disposed, in a central portion of the absorbent article for the pet in a longitudinal direction thereof; and
    a low stiffness region that is formed between the first high stiffness region and the second high stiffness region and is lower in bending stiffness than the first high stiffness region and the second high stiffness region,
    wherein an end portion of the elastic member is positioned at the low stiffness region.

3. The absorbent article for a pet according to claim 2, further comprising a locking member that is disposed on a back surface layer side of one of the pair of end portions and is configured in a rectangular shape, wherein a longitudinal direction of the locking member extends along the width direction of the absorbent article for the pet,
    wherein the first high stiffness region is formed in a part of the absorbent article for the pet in which the locking member is disposed in the one of the pair of end portions.

4. The absorbent article for a pet according to claim 1, wherein
    the absorbent core comprises: a belt-like absorbent core main body that extends from one end side to another end side of the absorbent article for the pet in a longitudinal direction; and a first extension portion that projects outwards in a width direction from a side edge of the belt-like absorbent core main body on a side of the first solid gather portion being disposed in a central portion of the absorbent core main body in the longitudinal direction.

5. The absorbent article for a pet according to claim 4, further comprising a position mark that indicates a position that can be used as an index when putting the absorbent article on the pet.

6. The absorbent article for a pet according to claim 5, wherein
    the position mark is disposed at a position corresponding to the absorbent article main body or the first extension portion.

7. The absorbent article for a pet according to claim 5, wherein the position mark is disposed at a position that is visually recognizable from an outer face side of the back surface layer.

* * * * *